United States Patent [19]

Takematsu et al.

[11] 4,448,601
[45] * May 15, 1984

[54] HERBICIDAL COMPOSITIONS AND HERBICIDAL PROCESSES

[75] Inventors: Tetsuo Takematsu; Makoto Konnai, both of Utsunomiya; Kunitaka Tachibana, Yokohama; Takashi Tsuruoka, Kawasaki; Shigeharu Inouye; Tetsuro Watanabe, both of Yokohama, all of Japan

[73] Assignee: Meiji Seika Kaisha, Ltd., Chuo, Japan

[*] Notice: The portion of the term of this patent subsequent to Jan. 5, 1999 has been disclaimed.

[21] Appl. No.: 334,042

[22] Filed: Dec. 23, 1981

Related U.S. Application Data

[63] Continuation of Ser. No. 959,838, Nov. 13, 1978.

[30] Foreign Application Priority Data

Mar. 9, 1978 [JP] Japan ................................. 53-25971

[51] Int. Cl.³ ............................................. A01N 71/86
[52] U.S. Cl. ........................................................ 71/86
[58] Field of Search ............................................. 71/86

[56] References Cited

U.S. PATENT DOCUMENTS

| | | | |
|---|---|---|---|
| 3,850,608 | 11/1974 | Hamm | 71/86 |
| 3,868,407 | 2/1978 | Franz | 71/86 |
| 4,002,672 | 1/1977 | Smith | 71/86 |
| 4,148,627 | 4/1979 | Maier | 71/86 |
| 4,197,254 | 4/1980 | Gaertner | 71/86 |
| 4,226,610 | 10/1980 | Takematsu | 71/86 |
| 4,262,727 | 4/1981 | Dutra | 71/86 |
| 4,309,208 | 1/1982 | Takematsu | 71/86 |

FOREIGN PATENT DOCUMENTS

| | | | |
|---|---|---|---|
| EP10066 | 4/1980 | European Pat. Off. | 71/86 |
| 2848224 | 8/1979 | Fed. Rep. of Germany | 71/86 |

*Primary Examiner*—Paul J. Killos
*Attorney, Agent, or Firm*—Haight & Associates

[57] ABSTRACT

A known antibiotic, SF-1293 substance and salts thereof have now been found to exhibit high herbicidal effects against a wide variety of herbaceous and woody plants, but they are non-phytotoxic particularly to a useful woody plant, *Chamaecyparis obtusa*. The herbicidal effects of these SF-1293 substances can be noticeably enhanced by applying in combination with certain known herbicides or compounds having biological activities.

3 Claims, No Drawings

HERBICIDAL COMPOSITIONS AND HERBICIDAL PROCESSES

This is a continuation of application Ser. No. 959,838, filed Nov. 13, 1978.

BACKGROUND OF THE INVENTION

1. Field of the Invention

This invention relates to herbicidal compositions, preparation thereof and processes of controlling unwanted plants using the herbicidal compositions.

2. Description of the prior art

All of the active substances which have hitherto been used as herbicide are the chemically synthetic compounds, which may sometime give rise to problems of environmental pollution. From a viewpoint of increasingly severe legal regulations of environmental pollution, the demand now increases to provide those herbicidal substances which can be rapidly decomposed in the surrounding conditions and cause no environmental contamination.

We described and claimed the antibiotic, SF-1293 substance and a microbiological process for the production thereof (see Japanese Pat. No. 827,768, U.S. Pat. No. 3,832,394 and German Pat. No. 2,236,599). It is now found that the SF-1293 substance as a herbicide can meet the requirements mentioned above since it is susceptible to metabolism and breakdown into harmless substances in the course of the material-circulation occurring in nature.

The SF-1293 substance (in the free acid form) is the compound of the formula:

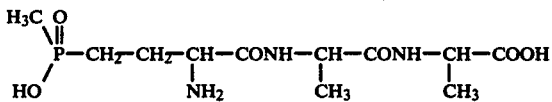

As described in the aforesaid U.S. and German Patents, the SF-1293 substance is highly active to various fungal diseases of plants, including *Pellicularia sasakii* (sheath blight on rice) and *Piricularia oryzae* (rice blast).

SUMMARY OF THE INVENTION

As a result of our further study of the biological activities and utilities of the SF-1293 substance, we have now found that it exhibits a considerably high herbicidal effect when applied at a rate of about ten times higher than that at which it has been used as fungicide. Thus, it has been found that the SF-1293 substance, and various salts whereof are herbicidally active to growing annual and perennial weeds as well as various bushes and trees, and that upon foliage treatment, they can severely damage or kill the overground segments of the plants and strongly inhibit regrowth of the plants from their underground rhizomes.

DETAILED DESCRIPTION OF THE INVENTION

According to a most generic aspect of this invention, therefore, there is provided a process of severely damaging or killing unwanted plants, which comprises applying to the plants or to the growth medium thereof, a herbicidally effective amount of the SF-1293 substance as defined in hereinafter or a salt thereof.

The SF-1293 substance (the free acid form) and salts thereof (hereinafter collectively referred to merely as "SF-1293 substances") are effective to severely damage or kill unwanted plants both when applied directly to the plants ("post-emergence application") and when applied to soil or other growth medium where the plants are growing, to prevent the emergence of seedlings of the plants ("pre-emergence application").

The SF-1293 substances for use in this invention are advantageous in that they may be applied at an optional time in all seasons and that they are effective not only as a contact herbicide but also as a translocated or systemic herbicide. Further, they have favorably the unique feature that they are non-phytotoxic to useful woody plant, *Chamaecyparis obtusa* (Japan cypress, "hinoki" in Japanese, which provides a wood material extensively used in the construction of furnitures and houses) but they are highly toxic to unwanted bushes and weeds growing in the area where the useful woody plants occur naturally or are cultivated artificially.

In a further aspect, therefore, this invention provides a process of selectively controlling the growth of weeds and bushes in the area of *Chamaecyparis obtusa*, which comprises applying to the area the SF-1293 substance or a salt thereof in an amount sufficient to inhibit the growth of the weeds and bushes.

In recent years, infestation of exotic and naturalized weeds and perennial weeds comes into question, and N-phosphonomethylglycin (which is usually known as glyphosate) is effectively used to control the growth of these weeds. It has been observed that the antibiotic SF-1293 substance, which acts similarly to glyphosate, is very superior to glyphosate in respect of the herbicidal properties and weed-control spectrum. Thus, as compared with the glyphosate, the SF-1293 substance is effective at a lower concentration, more rapidly develops the herbicidal effect and shows a much wider spectrum of weed control, and further it is absolutely non-phytotoxic towards *Chamaecyparis obtusa* as already stated. In contrast, glyphosate disadvantageously shows a phytotoxicity to *Chamaecyparis obtusa*. Besides, glyphosate is much less active to broadleaved weeds and perennial weeds such as *Rumex japonicus* and *Cayratia japonica*. While, the SF-1293 substance is equivalently active against the weeds irrespective of weed species at the same application rate and completely suppresses regrowth or recovery of perennial weeds.

Generally, non-crop land, orchard, forestry land and grassland can be infested with annual and perennial weeds and various bushes. In order to control the growth thereof, either treatment of applying a mixture of two or more herbicides at once or treatment of applying different or same herbicide(s) several times at intervals may be employed. Both of these herbicidal procedures, however, are very complicated and disadvantageous in the cost and labor involved therein. The SF-1293 substances are highly active against almost all weeds, bushes and trees except for *Chamaecyparis obtusa*, so that application of the SF-1293 substances alone can controll all of the undesired plants, inclusive of weeds and unwanted trees, as intended. Besides, the SF-1293 substances can prevent regrowth or recovery of the undesired plants, indicating that they are a herbicide of particular great value in practice. Thus, the SF-1293 substances are effectively applied for land preparation in forestry land, control of bottom weeds growing in forestry land of *Chamaecyparis obtusa*, control of weeds and bushes in grassland, bottom weed-control in orchard and inhibition of weed growth in non-crop land, and further they are suitable for presowing treatment in uncultivated upland, by utilizing their properties that they will become inactivated at a relatively high rate in soil. The SF-1293 substances are also suitable for "spot" herbicidal treatment in crop area or lawn area infested with vicious perennial weeds.

The SF-1293 substances used in the process of the invention are usually applied in the form of a composition comprising the SF-1293 substances as the active ingredient which is mixed with a liquid or solid diluent or carrier. In another aspect, therefore, this invention provides a herbicidal composition comprising as active ingredient at least one member selected from SF-1293 substance of the structural formula:

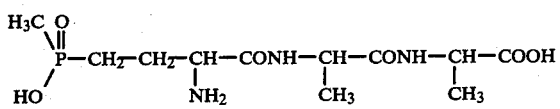

and salts thereof, in admixture with a diluent or carrier.

The composition of the invention may generally comprise the active ingredient in an amount of 0.01% to 50 % by weight of the composition. When applied to the herbicidal treatment, this composition usually may be diluted with water to a concentration of 0.05% to 5% with regard to the active ingredient.

The salts of the SF-1293 substance which may be used as the active ingredient according to this invention include an alkali metal salt, an alkaline earth metal salt, a divalent-metal salt, an unsubstituted or substituted ammonium salt or an acid-addition salt which may generally be represented by the following formula:

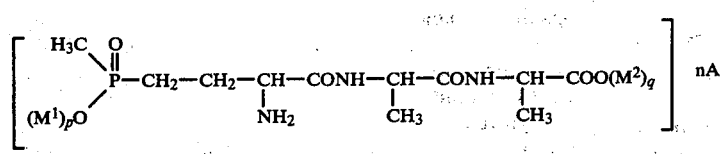

wherein $M^1$ and $M^2$, which may be the same or different, each represents hydrogen atom or a cation selected from sodium, potassium, lithium, copper, magnesium, calcium, zinc, nickel and manganese, or an ammonium cation either unsubstituted or substituted by one, two, three or four lower alkyl, hydroxy-lower alkyl, particularly hydroxyethyl or lower alkenyl group; A represents an inorganic or organic acid selected from hydrochloric, sulfuric, hydrobromic, phosphoric, perchloric, nitric, acetic, propionic, citric, tartaric, monochloroacetic, trichloroacetic and trifluoroacetic acids; and n is 0, ½ or 1, p is the inverse number of the valency of $M^1$, and q is the inverse member of the valency of $M^2$.

The composition of this invention may be in the form of aqueous solution, wettable powder, dusting powder, emulsion, granules or grains comprising the active ingredient in admixture with a suitable diluent or carrier.

The solid compositions may be in the form of dusting powders or granules. Suitable solid diluents include kaolin, clay, bentonite, kieselguhr, dolomite, calcium carbonate, talc, powdered magnesia, Fuller's earth, gypsum, Hewitt's earth, diatomaceous earth and vermiculite.

Solid compositions may also be in the form of dispersible powders or grains comprising a wetting agent to facilitate the dispersion in liquids of the powder or grains which may contain also fillers and suspending agents.

Liquid compositions include aqueous solution, dispersions or emulsions which may be prepared by dissolving the active ingredient(s) in an organic solvent optionally containing wetting, dispersing or emulsifying agent(s) and then adding the mixture to water which may also contain wetting, dispersing or emulsifying agent(s). Suitable solvents are acetone, isopropyl alcohol, propylene glycol, diacetone alcohol, benzene, toluene, kerosene, methylnaphthalene and cyclohexanone.

By including suitable additives, for example, additives for improving the distribution, adhesive power and resistance to rain on treated surfaces, the different compositions can be better adapted for intended purposes.

The compositions of the invention can comprise also other herbicides or plant-growth regulators known per se, for example, germination inhibitors so as to envisage enhancement of the herbicidal effect of the SF-1293 substances and extension of a period during which the substances remain active.

The compositions of the invention may also be in the form of liquid preparations for use as sprays which are generally aqueous dispersions or emulsions containing the active ingredient in the presence of one or more wetting agent(s), dispersing agent(s), emulsifying agent(s) or suspending agent(s). These agents can be cationic, anionic, non-anionic or ampholytic agents.

Suitable cationic agents are quaternary ammonium compounds, for example, cetyltrimethylammonium bromide and alkylpyridinium chloride. Suitable anionic agents are soaps, salts of aliphatic monoesters of sulphuric acid (for example sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropylnaphthalene sulphonates). Suitable non-ionic agents are the condensation products of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene oxide, and the lecithins. Suitable ampholytic agents are alkyldimethyl betaine and dodecylaminoethyl glycine. Suitable suspending agents are hydrophilic colloids (for example, polyvinylpyrrolidone and sodium carboxymethylcellulose), and the vegetable gums (for example, gum acacia and gum tragacanth).

The compositions for use as aqueous dispersions or emulsions are generally supplied in the form of a concentrate containing a high proportion of the active ingredient, the concentrate being diluted with water before use. These concentrates often should be able to withstand storage for prolonged periods and after such storage be capable of dilution with water in order to form aqueous preparations which remain homogeneous for a sufficient time to enable them to be applied by conventional spray equipment.

The SF-1293 substance to be used as the active ingredient can be produced, as described in the specifications of U.S. Pat. No. 3,832,394 and German Pat. No. 2,236,599, by a microbiological process comprising cultivating a SF-1293 substance-producing strain of *Streptomyces hygroscopicus* under aerobic conditions to produce and accumulate the SF-1293 substance in the culture broth and recoving the active substance from the culture broth. A typical example of the SF-1293 substance-producing strain of *Streptomyces hygroscopicus* is a strain designated as *Streptomyces hygroscopicus* SF-1293 which has been deposited in the American Type Culture Collection under ATCC No. 21705 and in Japanese public depository "Fermentation Research Institute" under FERM-P No. 996. The salts of the SF-1293 substance may be prepared by any convenient salt-forming method.

The rate of application of the SF-1293 substances required to control unwanted plants will depend upon the identity of the plant species and the particular active compound selected for use as well as the climate conditions. However, in general, an application rate of 25 g. to 3000 g. per 10 ares is used. Our experiments have shown that it is most efficient for the herbicidal purpose to apply at a rate of about 100 l per 10 ares the liquid composition containing 0.01% to 0.05% by weight of the active ingredient to weeds of less than 10 cm in height or the liquid composition containing 0.05% to 0.2% by weight of the active ingredient to weeds of 10 to 30 cm in height.

As stated hereinbefore, the SF-1293 substances are defective not only as the contact herbicide but as the translocated or systemic herbicide, thereby achieving the regrowth-inhibitory effect which is most important for control of perennial weeds and bushes.

We have made great endeavors to utilize the inherent, advantageous features of the SF-1293 substances to a maximum, and as a consequence we have discovered that the herbicidal effects of the SF-1293 substances can be appreciably improved when they are applied in combination with one or more known herbicides or other biologically active substances, and particulary in combination with one or more translocated herbicides or relatively slow-acting herbicides.

According to a still further aspect of this invention, therefore, there is provided a herbicidal composition comprising as active ingredient a mixture of:

(A) at least one member selected from the SF-1293 substance and salts thereof, and (B) at least one member selected from choline salt of maleic hydrazide (hereinafter referred to as CMH); phenoxy herbicides; benzoic herbicides; 2,3,-trichlorophenylacetic acid (hereinafter referred to as TPA) and its salts; [(3,5,6-trichloro-2-pyridyl)-oxy]acetic acid (hereinafter referred to as Dowco-233) and its salts; n-phosphonomethylglycine (usually denoted as glyphosate) and its salts; ethyl carbamoylphosphate (hereinafter referred to as DPX-1108) and its salts; 2-(1-allyloxyamino)-butylidene-5,5-dimethyl-4-methoxycarbonyl-cyclohexane-1,3-dione (referred to as NP-48); 3-(3,4-dichlorophenyl)-1-methoxy-1-methylurea (hereinafter denoted as Linuron); 3-amino-1,2,4-triazole (hereinafter referred to as ATA); cholines; and diethylamines.

The phenoxy herbicides include, for example, 2,4-dichlorophenoxyacetic acid (hereinafter referred to as 2,4-D) and salts, allyl ester and ethyl ester thereof, 2-methyl-4-chlorophenoxyacetic acid (hereinafter referred to as MCP) and salts, allyl ester and ethyl ester thereof, α-(3,4-dichlorophenoxy) propionic acid (hereinafter referred to as 3,4-DP) and its salts, d,l-2-(2-methyl-4-chlorophenoxy) propionic acid (hereinafter denoted as MCPP) and its salt, γ-(2-methyl-4-chlorophenoxy) acetic acid (hereinafter denoted as MCPP) and its salt, d,l-2-(2,4,5-trichlorophenoxy) propionic acid (hereinafter denoted as 2,4,5-P) and its salts, and α-[4-(3,5-dichloropyridyl-2-oxy)]phenoxypropionic acid (hereinafter denoted as SL-501) and its salts.

The benzoic herbicides include, for example, 2,3,6-trichlorobenzoic acid (hereinafter referred to as TBA) and its salts, 3,6-dichloro-2-methoxybenzoic acid (hereinafter referred to as Banvel-D) and its salts and 3-amino-2,5-dichlorobenzoic acid (hereinafter referred to as Amiben) and its salts.

The cholines include choline itself and choline salts, examples of which are salts of choline with an inorganic acid such as hydrochloric acid, phosphoric acid and carbonic acid or an organic acid such as acetic acid, oxalic acid and ascorbic acid.

The diethylamines include diethylamine itself and its salts, examples of which are the salt with an inorganic or organic acid same as mentioned above for the choline salts.

The salts of the SF-1293 substance which may be used in combination with the component (B) typically include those of the general formula (1) as defined hereinbefore.

Our extensive studies on mixtures of the SF-1293 substances with other agents have revealed the following:

Firstly, the herbicidal activity of the SF-1293 substances may be significantly enhanced when they are applied in combination with a wide variety of herbicides or synergists. In particular, a combination with a translocated herbicide or relatively slow-acting herbicide leads to maximum improvement in the herbicidal effect of the SF-1293 substances.

By way of example, as will be seen from Table 8 given hereinbelow, application of 100 1/10 ares of a solution containing monosodium salt of the SF-1293 substance used alone at 0.05% concentration gives about 50% kill to *Rumex obtusifolius* (one of broad-level weeds) but cannot bring about suppression of regrowth of this weed, whereas application of 100 1/10 ares of a solution containing 2,4-D at 0.1% concentration allows only bending of the stem and foliage of *Rumex obtusifolius* but does not exhibit the effect of killing or suppression of regrowth of this weed. In contrast, the application of 100 1/10 ares of a solution containing in combination SF-1293 monosodium salt at 0.05% concentration and 2,4-D at 0.1% concentration achieves earlier development and pronounced enhancement of the herbicidal effect of the SF-1293 monosodium salt, resulting in complete kill of the overground segments but in no regrowth from the underground rhizomes of this weed. The same can be observed for *Zoysia japonica* which is one of graminaceous perennial weeds. Thus, application of a solution containing SF-1293 monosodium salt at 0.1% concentration gives about 50% kill to *Zoysia japonica* but allows the regrowth to take place to an extent comparable to the untreated plot at the lapse of three months after the treatment. While, application of a solution containing 2,4-D at 0.1% concentration exhibits slight or substantially no activity to graminaceous plants. On the other hand, the application of a solution containing in combination 0.1% SF-1293 monosodium salt and 0.1% 2,4-D achieves complete kill and no regrowth whatsoever at the lapse of three months after treatment, owing to the synergistically increased activity of the SF-1293 sodium salt. Thus, the combined use of the SF-1293 substances and a biologically active substance with auxin activity (of which 2,4-D is representative) can lead to salient improvement in the contact and systemic, herbicidal activities of the SF-1293 substances towards both broad-leaved perennial weeds and graminaceous perennial weeds and bring about extremely improved effect of inhibiting the regrowth of the weeds.

Such noticeable improvements have been achieved also when CHM which is known as one of the anti-auxins is applied in combination with the SF-1293 substances, as illustrated in Examples 9–15. Whilst the use of CMH alone exhibits a very poor herbicidal activity to weeds at growth stage, the combined use of CMH and the SF-1293 substances leads to a characteristic advantage that the contact herbicidal effect as well as the regrowth-inhibitory effect by translocation of the SF-1293 substances are improved remarkably. For instance, in Example 9, the combined use of the SF-1293 substances at 0.05% concentration and CMH at 0.3% concentration resulted in enhancement of both the contact herbicidal effect (when evaluation is made 21 days after the herbicidal treatment) and the regrowth-inhibitory effect (when evaluation is made 4 months after the herbicidal treatment), as compared to the case when the SF-1293 substances is used alone at 0.1% concentration. Generally, the use of the SF-1293 substance and CMH in combination allows the effect of the SF-1293 substances to be improved by twice and even by four to five times.

In addition, we have found that other various, biologically active compounds are effective to improve the activity of the SF-1293 substances. Among these, the synergism as discussed above has been observed with the compounds listed as the Component (B) as stated hereinbefore, and this will be clear from Table 8.

Secondly, the SF-1293 substances exhibit a wider spectrum of weed control when they are applied in combination with the compounds (B), as shown in Examples 11–15. In order to ensure that the SF-1293 substances can achieve to the utmost the effect of inhibiting the regrowth of perennial weeds, it is necessary that they should translocate and migrate into the underground segments of the weed plant after foliage treatment but before killing of the foliage occurs. In the herbicidal treatment of plants such as *Calystegia hederacea* which are very susceptible of the contact herbicidal effect of the herbicide applied thereto, it is difficult to inhibit regrowth of this weed from the underground rhizomes due to that killing of the foliage takes place before the SF-1293 substances commence their translocation and migration into the underground rhizomes. Nevertheless, the combined use of the SF-1293 substances and the compounds (B) enhances the translocated herbicidal activity and thus strongly inhibits even regrowth of such plants as *Calystegia hederacea* because the combined use of the compounds (A) and (B) can achieve the migration of the active agents into the underground rhizomes prior to killing of the foliage. All of the compounds (B) enable extension of weed-control spectra of the SF-1293 substances when they are applied in combination therewith. In particular, best results can be obtained by combination of the SF-1293 substances with CMH as shown in Examples 11–15.

It is known that CMH may suppress regrowth of perennial weeds when it is applied in autumn season (see Japanese Patent Preliminary Publication No. 55835/76). In practical use, however, CMH has the drawback that it can be normally applied only in autumn season, and that the overground segments of perennial weeds must be removed out by moving when CMH is applied in spring or summer season for the herbicidal purpose. As opposed to CMH used alone, when CMH is applied in admixture with the SF-1293 substances, the latter gradually kill the overground segments while both CMH and the SF-1293 substances translocate into and kill the underground segments of the perennial weeds by the synergistic effect, resulting in complete suppression of regrowth of these weeds. It has thus been observed that the combined application of CMH and the SF-1293 substances ensures the regrowth-inhibiting ability of CMH to display to a satisfactory extent and enables CMH to be applied effectively throughout all seasons, which significantly improves the practical utility of CMH.

Thirdly, the SF-1293 substances have no phytotoxicity to a useful tree, *Chamaecyparis obtuse* which dominates 25% of the area of the forestry land in Japan, and CMH is also non-toxic to the same. Accordingly, application of a formulation comprising a mixture of the SF-1293 substances and CMH to the area of *Chamaecyparis obtusa* (Japan cypress) resulted in efficient control of unwanted plants, particularly perennial weeds and bushes which are concurrently growing in said area. Besides, CMH, CPX-1108, cholines and diethylamines are likewise non-toxic to the cypress plant.

The compositions comprising a mixture of the SF-1293 substances and the compounds (B) can be applied for various herbicidal purposes in many areas and lands including crop area, forestry land, grassland, orchard and non-crop land, as previously described for the compositions comprising the SF-1293 substances alone as active ingredient. Further, the compositions may be applied in aquatic areas to control aquatic weeds and algae as well as in aquatic rice plant field after the harvest of the ripened rice plants.

The ratio of the SF-1293 substances (A) to the compounds (B) to be incorporated in the compositions may vary over a wide range depending upon the nature of the compounds (B) and the envisage use of the compositions. By way of general guidance, however, this mixing ratio may be in the range from 1:0.2 to 1:20 by weight. Usually, the weight ratio of the SF-1293 substances to each of the compounds (B) may be as shown in Table 1 below.

The total amount of the SF-1293 substance (A) and the compounds (B) in the herbicidal compositions of this invention may generally be in a range of 0.05% to 80% by weight of the whole compositions. Upon use, the composition may usually be diluted to an active ingredient concentration of 0.05% to 5% by weight. The amount of the SF-1293 substance applied usually may then be in a range of 25 g to 1500 g per 10 ares.

The compositions comprising the respective active compounds at concentrations indicated in Table 1 may be applied generally at a rate of 25 to 250 l, preferably 50 to 150 l per 10 ares.

TABLE 1

| Active Ingredient | Mixing Ratio | Concentration (%) in formulation to be applied |
|---|---|---|
| SF-1293 substances | 1 | 0.01–1.0 |
| SF-1293 substances:CMH | 1:1.0–20.0 | 0.01–1.0:0.2–1.0 |
| SF-1293 substances:2,4-D | 1:0.3–8.0 | 0.01–1.0:0.05–0.5 |
| SF-1293 substances:MCP | 1:0.3–5.0 | 0.01–1.0:0.05–0.5 |
| SF-1293 substances:3,4-DP | 1:0.5–8.0 | 0.01–1.0:0.05–0.5 |
| SF-1293 substances:MCPP | 1:0.3–5.0 | 0.01–1.0:0.05–0.5 |
| SF-1293 substances:MCPB | 1:0.3–5.0 | 0.01–1.0:0.05–0.5 |
| SF-1293 substances:2,4,5-T | 1:0.3–5.0 | 0.01–1.0:0.05–0.5 |
| SF-1293 substances:SL-501 | 1:0.5–10.0 | 0.01–1.0:0.05–0.5 |
| SF-1293 substances:2,3,6-TBA | 1:0.3–5.0 | 0.01–1.0:0.05–0.5 |
| SF-1293 substances:Banvel-D | 1:0.3–5.0 | 0.01–1.0:0.05–0.5 |
| SF-1293 substances:Amiben | 1:0.3–5.0 | 0.01–1.0:0.05–0.5 |
| SF-1293 substances:TPA | 1:0.3–5.0 | 0.01–1.0:0.05–0.5 |
| SF-1293 substances: Dowco-233 | 1:0.2–6.0 | 0.01–1.0:0.02–0.2 |
| SF-1293 substances: Glyphosate | 1:0.3–5.0 | 0.01–1.0:0.03–0.5 |
| SF-1293 substances:DPX-1108 | 1:0.5–10.0 | 0.01–1.0:0.1–0.6 |
| SF-1293 substances:NP-48 | 1:0.5–10.0 | 0.01–1.0:0.05–0.5 |
| SF-1293 substances:Lynuron | 1:0.5–10.0 | 0.01–1.0:0.05–0.5 |
| SF-1293 substances:ATA | 1:0.3–5.0 | 0.01–1.0:0.05–0.5 |
| SF-1293 substances:Cholines | 1:1.0–2.4* | 0.01–1.0:0.01–0.8 |
| SF-1293 substances: Diethylamines | 1:1.0–2.4* | 0.01–1.0:0.01–0.5 |

An asterisk (*) indicates molar ratio.

The amount of the SF-1293 substances to be used to kill perennial weeds and bushes and to inhibit regrowth thereof will be affected also by the surrounding climatic conditions, for example, temperature and intensity of light. By way of example, however, the purposes envisage can be obtained by applying the SF-1293 substances at a rate of: 25 to 600 g per 10 ares for perennial weeds of 1 m or less in height (e.g. *Artemisia princeps, Rumex japonicus, Cyperus rotundus* etc.); 75 to 750 g/10 ares for perennial weeds of 1 or more in height (e.g. *Sasa nipponica, Miscanthus sinensis* etc.) and small bushes (e.g. *Rhododendron haempferi, Rubus crataegifolins* etc.); and 150 to 1500 g/10 ares for big bushes (e.g. *Castanea crenata, Quercus serrata* etc.) as well as for control of fresh sprouts from big stumps.

The compositions comprising the mixed active compounds (A) and (B) can be formulated into any conventional form, including aqueous solution, dusting powder, wettable powder, emulsion, granule and grain using any known solid or liquid diluent or carrier by any convenient method, as detailed hereinbefore.

This invention is further illustrated but not limited by the following Examples in which percentages (%) are all by weight unless otherwise stated. In the Examples mono-substituted salts of SF-1293 substance are essentially in the form of the corresponding phosphate (only $M^1$ in the above formula (I) is a cation and $M^2$ is a hydrogen atom).

Examples 1–3 illustrate the preparation of the compositions according to the invention.

EXAMPLE 1

| Aqueous solution | | |
|---|---|---|
| (1a) | SF-1293 substance (free acid) | 30.00% |
| | Octylphenylpolyoxyethanol | 10.00% |
| | Methyl para-hydroxybenzoate | 0.15% |
| | Water | 54.85% |
| (1b) | Monosodium salt of SF-1293 substance | 10.00% |
| | CMH | 20.00% |
| | Octylphenylpolyoxyethanol | 15.00% |
| | Methyl para-hydroxybenzoate | 0.15% |

| Aqueous solution | |
|---|---|
| Water | 54.85% |

The ingredients listed in above 1(a) and 1(b), respectively, were mixed together to prepare an aqueous solution which may be diluted with water for use in the foliage treatment.

EXAMPLE 2

| Wettable powder | | |
|---|---|---|
| (2a) | SF-1293 substance (free acid) | 50.0% |
| | Kieselguhr | 45.0% |
| | Monosorbitan alkylester (as surfactant) | 5.0% |
| (2b) | Mono (diethanolamine) salt of SF-1293 substance | 15.0% |
| | 2,4-D (Na-salt) | 30.0% |
| | Kieselguhr | 50.0% |
| | Monosorbitan alkylester | 5.0% |

The ingredients listed above in 2(a) and 2(b), respectively, were together mixed uniformly in the proportions indicated and ground finely to prepare wettable powders, which are readily dispersible in water and used as, for example, sprays for foliage treatment.

EXAMPLE 3

| Dusting powder | | |
|---|---|---|
| (3a) | SF-1293 substance (free acid) | 5% |
| | Talc | 95% |
| (3b) | Monoisopropylamine salt of SF-1293 substance | 5.0% |
| | Dowco-233 (Na salt) | 5.0% |
| | Talc | 90.0% |

Compositions in the form of dusting powder were prepared by mixing and grinding uniformly all the ingredients listed in above 3(a) and 3(b), respectively, in the proportions stated. The dusting powder may be directly applied for foliage treatment at a rate of 0.4 to 6 kg per 10 ares.

Examples 4–8 illustrate the herbicidal properties of the SF-1293 substances.

EXAMPLE 4

(Pre-emergence test)

Upland soil was placed in a pot of 10 cm diameter and seeds of *Digitaria adscendens* (Crabgrass) were sown in the soil at a depth of 1 cm. After gently pressing the soil surface, the soil was sprayed evenly with solutions of SF-1293 substance sodium salt dissolved at different concentrations in 5 cc of water. 10 Days after spraying, the number of the seedlings of crabgrass was counted and percentage (%) of prevention of emergence was evaluated by comparison with untreated plots. For comparison, the tests were also conducted using glyphosate instead of the SF-1293 sodium salt. The results are shown in Table 2 below.

TABLE 2

| Test Compounds | Prevention (%) of Emergence Rate of Application g/10a | | | |
|---|---|---|---|---|
| | 0 | 100 | 250 | 500 |
| SF-1293 substance | 0 | 95 | 100 | 100 |

TABLE 2-continued

| Test Compounds | Prevention (%) of Emergence Rate of Application g/10a | | | |
|---|---|---|---|---|
| | 0 | 100 | 250 | 500 |
| (Na salt) Glyphosate (isopropyl-amine salt) (Control) | 0 | 0 | 0 | 0 |

EXAMPLE 5

(Post-emergence test)

Upland soil was placed in a pot of 10 cm diameter and seeds of crabgrass were sown in the soil at a depth of 1 cm from the soil surface. When the seedlings grew to a height of about 10 cm, 1.2 ml (equivalent to 100 l/10a) of aqueous solutions of the test compounds at different concentrations as indicated in Table 3 below were applied evenly for foliage treatment. 10 Days after treatment, damage to plants was visually assessed on a scale of 0 to 10 where 0 indicates no effect and 10 indicates complete kill.

The detail of this assessment made in this Example was as follows:

| Scale | Foliage Damage (%) |
|---|---|
| 0 | 0% |
| 1 | 10% |
| 2 | 20% |
| 3 | 30% |
| 4 | 40% |
| 5 | 50% |
| 6 | 60% |
| 7 | 70% |
| 8 | 80% |
| 9 | 90% |
| 10 | 100% |

The test results are tabulated in Table 3.

TABLE 3

| Test Compound | Damage Scale Concentration (ppm) | | | |
|---|---|---|---|---|
| | 0 | 0.01 | 0.03 | 0.1 |
| SF-1293 substance (Na salt) | 0 | 1 | 8 | 10 |
| SF-1293 substance (dimethylamine salt) | 0 | 3 | 10 | 10 |
| Glyphosate (isopropyl-amine salt) (Control) | 0 | 0 | 5 | 10 |

The above Table shows that an improved herbicidal effect is exhibited by an organic amine salt of SF-1293 substance.

EXAMPLE 6

Aqueous solutions containing sodium salt of SF-1293 substance at different concentrations as indicated in Table 4 below and 0.1% of actylphenylpolyoxyethanol as surfactant were prepared and applied at a rate of 150 l per 10 ares directly to spontaneously occurring perennial weeds at growth stages indicated in Table 4. 7 Days and 14 days after foliage treatment, damage to the plants was vissually assessed on a scale of 0 to 5 where 0 signifies no effect and 5 signifies complete kill.

The detail of this assessment made in this Example was as follows:

| Scale | Foliage Damage (%) |
|---|---|
| 0 | 0 |
| 1 | 20% |
| 2 | 40% |
| 3 | 60% |
| 4 | 80% |
| 5 | 100% |

One month after treatment, evaluation was made for inhibition of regrowth expressed in terms of symbols ranging from (−) to (+++) where (−) means no regrowth, namely complete suppression of regrowth, (±) remarkable suppression of regrowth; (+) considerable suppression of regrowth; (++) medium suppression of regrowth; and (+++) no suppression of regrowth.

The results are set forth in Table 4.

In the Tables given hereinafter, "SF-1293" means monosodium salt of SF-1293 substance.

TABLE 4

| Test Plants | Growth Stage (cm) | Damage Scale | | | | | | | Scale of Regrowth Suppression | | | |
|---|---|---|---|---|---|---|---|---|---|---|---|---|
| | | 7 Days | | | | 14 Days | | | | 1 Month | | |
| | | SF-1293 (Na salt) | | Glyphosate (isopropyl-amine salt) | | SF-1293 (Na salt) | | Glyphosate (isopropyl-amine salt) | | SF-1293 (Na salt) | | Glyphosate (isopropyl-amine salt) | |
| | | 0.1% | 0.2 | 0.1 | 0.2 | 0.1 | 0.2 | 0.1 | 0.2 | 0.1 | 0.2 | 0.1 | 0.2 |
| Pc | 100 | 4 | 5 | 1 | 2 | 4 | 5 | 2 | 3.5 | − | − | + | ± |
| Ht | 70 | 4.5 | 5 | 3 | 4 | 5 | 5 | 4 | 5 | − | − | − | − |
| Ap | 50 | 5 | 5 | 3 | 4.5 | 5 | 5 | 3 | 4.5 | − | − | − | − |
| Cy | 30 | 4 | 5 | 1 | 2 | 5 | 5 | 1 | 2 | − | − | + | + |
| Ro | 30 | 4 | 5 | 1 | 2 | 5 | 5 | 2 | 3 | − | − | + | + |
| Ic | 80 | 4 | 5 | 1 | 1.5 | 5 | 5 | 1.5 | 3 | − | − | + | − |
| Pr | 5 m | 4 | 5 | 2 | 3 | 5 | 5 | 3 | 4 | − | − | − | − |
| Ms | 120 | 4 | 5 | 0.5 | 1 | 4 | 5 | 2 | 3.5 | − | − | + | − |

The names of the test plants are assigned as follows:
Pc: *Pleioblastus chino*
Ht: *Helianthus tuberosus*
Ap: *Artemisia princeps*
Cy: *Cayratia japonica*
Ro: *Rumex obtusifolius*
Ic: *Imperata cyrindrica*
Pr: *Pueraria lobata*
Ms: *Miscanthus sinensis*

As seen from Table 4, application of 150 l/10a of a solution containing SF-1293 substance at a concentration of 0.1–0.2% to spontaneous perennial weeds at the growing stage achieved complete kill thereof irrespective of weed species as well as complete suppression of regrowth.

EXAMPLE 7

Aqueous solutions containing sodium salt of SF-1293 substance at different concentrations indicated in Table 5 below and 0.1% of octylphenylpolyoxyethanol as surfactant were applied at a rate of 150 l/10a to the area where various bushes were spontaneously growing. One month after foliage treatment, damage to plants was visually assessed on a scale of 0 to 5 where 0 signifies no effect and 5 signifies complete kill as described in Example 6.

The results are set out in Table 5.

TABLE 5

| Test Compounds | Concentration | Overall Evaluation | Sc | Ct | Rb | Zp | Pa | Vb |
|---|---|---|---|---|---|---|---|---|
| SF-1293 (Na salt) | 0.1% | 4 | 4 | 4 | 5 | 4 | 4 | 4 |
| SF-1293 (Na salt) | 0.2 | 5 | 5 | 5 | 5 | 5 | 5 | 5 |
| SF-1293 (Na salt) | 0.3 | 5 | 5 | 5 | 5 | 5 | 5 | 5 |
| Glyphosate (isopropyl-amine salt) | 0.1 | 2 | 1.5 | 0.5 | 1 | 0 | 3 | 2 |
| Glyphosate (isopropyl-amine salt) | 0.2 | 3 | 4 | 0.5 | 1.5 | 1 | 4 | 3 |
| (Glyphosate (isopropyl-amine salt) | 0.3 | 4 | 4.5 | 1.5 | 2 | 2 | 4.5 | 3.5 |
| Untreated | | 0 | 0 | 0 | 0 | 0 | 0 | 0 |

The names of the plant species are assigned as follows:
Sc: *Smilax china*
Ct: *Castanea crenata*
Rb: *Rubus palmatus*
Zp: *Zanthoxylum piperitum*
Pa: *Pteridium aquilinum*
Vb: *Viburnum dilatatum*

Table 5 shows that SF-1293 substance also exhibits a high herbicidal activity against woody plants irrespective of plant species.

Example 8

Aqueous solutions containing sodium salt of SF-1293 substance at different concentrations indicated in Table 6 below and 0.1% of octylphenylpolyoxyethanol as surfactant were applied at a rate of 150 l/10a to woody plants of about 60–70 cm in height. 7 Days and 14 days after treatment, damage to test plants was visually assessed on the same scale (0 to 5) as stated in Example 7. The results are tabulated in Table 6.

TABLE 6

| Test Compounds | Concentration | 7 Days Pd | La | Ch | Cp | Ct | 14 Days Pd | La | Ch | Cp | Ct |
|---|---|---|---|---|---|---|---|---|---|---|---|
| SF-1293 (Na salt) | 0.125% | 3.5 | 4.5 | 0 | 0 | 5 | 5 | 5 | 0 | 0 | 5 |
| SF-1293 (Na salt) | 0.25% | 4 | 4.5 | 0 | 0.5 | 5 | 5 | 5 | 0 | 1 | 5 |
| SF-1293 (Na salt) | 0.5% | 4 | 4.5 | 0 | 0.5 | 5 | 5 | 5 | 0 | 2 | 5 |
| Glyphosate (isopropyl-amine salt) | 0.125% | 0 | 1 | 0 | 0 | 2 | 2 | 2 | 1 | 1 | 3 |
| Glyphosate (isopropyl-amine salt) | 0.25% | 1 | 1 | 0 | 1 | 2 | 3 | 3 | 3 | 3 | 4 |
| Glyphosate (isopropyl-amine salt) | 0.5% | 2 | 2 | 1 | 2 | 3 | 4 | 4 | 4 | 5 | 5 |
| Untreated | | 0 | 0 | 0 | 0 | 0 | 0 | 0 | 0 | 0 | 0 |

The names of the test plants are assigned as follows:
Pd: *Picea densiflora*
La: *Larix leptolepis*
Ch: *Chamaecyparis obtusa*
Cp: *Cryptomeria japonica*
Ct: *Castanea crenata*

As is observed from Table 6, SF-1293 substance is non-phytotoxic towards *Chamaecyparis obtusa* even upon the application of 150 l/10a of a solution containing the SF-1293 at a concentration of 0.5%, and thus it can be used to selectively control weeds and bushes in the forestry area of the useful plant.

Examples 9–15 illustrates the synergistic effects achieved by the combined use of the SF-1293 substances (A) and the active compounds (B) as well as the herbicidal effects of the SF-1293 substances used alone.

EXAMPLE 9

Formulations in the form of aqueous solution were prepared comprising as active ingredient different salts of SF-1293 substance (0.05% or 0.1%) or CMH(0.3%) or mixtures thereof and 0.1% of octylphenylpolyoxyethanol as surfactant. The aqueous solutions were applied at a rate of 100 l per 10 ares to *Rumex obtusifolius* at certain growth stage which was transplanted into pots of 20 cm in diameter. 21 Days after foliage treatment, damage to the test plant was visually assessed on a scale of 0 to 5 where 0 is no effect and 5 is complete kill as described in Example 6. 4 Months after treatment, further assessment was made both for damage to the plant and for suppression of regrowth from the underground rhizomes which is expressed in terms of symbols ranging from (−) to (+++) where (−) means complete suppression of regrowth and (+++) means maximum regrowth observed as described in Example 6.

The test results are shown in Table 7 below.

TABLE 7

| | 21 Days | | 4 Months | |
|---|---|---|---|---|
| | Concentration of SF-1293 substance salt | | | |
| Test Compounds | 0.05% | 0.1% | 0.05% | 0.1% |
| SF-1293 mono-Na salt | 2.5 | 3.5 | 0 +++ | 2.5 ++ |
| SF-1293 di-Na salt | 2.5 | 3.5 | 0 +++ | 2.5 ++ |
| SF-1293 mono-K salt | 2.5 | 3.5 | 0 +++ | 2.5 ++ |
| SF-1293 di-K salt | 2.5 | 3.5 | 0 +++ | 2.5 ++ |
| SF-1293 mono(isopropyl-amine) salt | 3 | 4 | 0 +++ | 3 + |
| SF-1293 mono(n-butylamine) salt | 3 | 4 | 0 +++ | 3 + |
| CMH (0.3%) | 1 | | 0 +++ | 0 |
| SF-1293 mono-Na salt + CMH (0.3%) | 4 | 4.5 | 4.5 ± | 5 − |
| SF-1293 di-Na salt + CMH (0.3%) | 4 | 4.5 | 4.5 ± | 5 − |
| SF-1293 mono-K salt + CMH (0.3%) | 4 | 4.5 | 4.5 ± | 5 − |
| SF-1293 di-K salt + CMH (0.3%) | 4 | 4.5 | 4.5 ± | 5 − |
| SF-1293 mono(isopropyl-amine) salt + CMH (0.3%) | 4.5 | 5 | 5 − | 5 − |

TABLE 7-continued

| | Scales | | | |
|---|---|---|---|---|
| | 21 Days | | 4 Months | |
| | Concentration of SF-1293 substance salt | | | |
| Test Compounds | 0.05% | 0.1% | 0.05% | 0.1% |
| SF-1293 mono(n-butyl-amine) salt + CMH (0.3%) | 4.5 | 5 | 5 | 5 |
| Untreated | 0 | | 0 | +++ |

As is seen from Table 7, the SF-1293 substances used alone at a concentration of 0.05% to 0.1% cannot achieve satisfactory suppression of regrowth and CMH used alone exhibits neither herbicidal effect nor re-growth-inhibitory effect. However, the combined use of the SF-1293 substance and CMH brings about a pronounced synergistic effect, thereby killing the overground and underground segments of the plant, with inhibiting regrowth from the underground rhizomes.

EXAMPLE 10

Aqueous solution containing the SF-1293 substances (A) and the components (B), in admixture or separately, at different concentrations indicated in Table 8 below were applied at a rate of 100 l per 10 ares to *Rumex obtusifolius* (abbreviated as Ro) and one of graminaceous perennial weeds, *Zoysia japonica* (abbreviated as Zy) which had been transplanted into pots at certain growth stage and taken root firmly in the pots. 21 Days after foliage treatment, damage to plants was visually assessed on a scale of 0 to 5 where 0 is no effect and 5 is complete kill as described in Example 6. 3 Months later, further assessment was made for suppression of regrowth based on the degree of killing the underground segments which is expressed in terms of the same symbols as stated in Example 9.

The results are set forth in Table 8, where monosodium salt of SF-1293 substance is abbreviated as "SF".

TABLE 8

| | Scales | | | |
|---|---|---|---|---|
| | 21 Days later | | 3 Months later | |
| Test Compounds (Concentration in %) | Ro | Zy | Ro | Zy |
| SF (0.05%) | 2.5 | 1.5 | +++ | +++ |
| SF (0.1%) | 3.5 | 2.5 | +++ | +++ |
| CMH (0.3%) | 0 | 0 | +++ | ++* |
| CMH (0.6%) | 0 | 0 | +++ | +* |
| CMH (0.3%) + SF (0.05%) | 4.5 | 3.5 | — | — |
| CMH (0.3%) + SF (0.1%) | 4.5 | 4 | — | — |
| CMH (0.6%) + SF (0.05%) | 5 | 5 | — | — |
| CMH (0.6%) + SF (0.1%) | 5 | 5 | — | — |
| 2,4-D (Na salt) (0.1%) | 1 | 0 | +++ | +++ |
| 2,4-D (Na salt) (0.2%) | 2 | 0 | +++ | ++* |
| 2,4-D (Na salt) (0.1%) + SF (0.05%) | 5 | 3.5 | — | + |
| 2,4-D (Na salt) (0.1%) + SF (0.1%) | 5 | 4 | — | — |
| 2,4-D (Na salt) (0.2%) + SF (0.05%) | 5 | 4.5 | — | — |
| 2,4-D (Na salt) (0.2%) + SF (0.1%) | 5 | 5 | — | — |
| MCP (Na salt) (0.1%) | 1 | 0 | +++ | +++ |
| MCP (Na salt) (0.2%) | 2 | 0 | +++ | +++ |
| MCP (Na salt) (0.1%) + SF (0.05%) | 4.5 | 3 | + | + |
| MCP (Na salt) (0.1%) + SF (0.1%) | 4.5 | 4 | ± | ± |
| MCP (Na salt) (0.2%) + SF (0.05%) | 5 | 5 | — | — |
| MCP (Na salt) (0.2%) + SF (0.1%) | 5 | 5 | — | — |
| 3,4-DP (Na salt) (0.1%) | 1 | 0 | +++ | +++ |
| 3,4-DP (Na salt) (0.2%) | 2 | 0 | +++ | +++ |
| 3,4-DP (Na salt) (0.1%) + SF (0.05%) | 4 | 3 | + | + |
| 3,4-DP (Na salt) (0.1%) + SF (0.1%) | 4 | 4.5 | ± | ± |
| 3,4-DP (Na salt) (0.2%) + SF (0.05%) | 5 | 5 | — | — |
| 3,4-DP (Na salt) (0.2%) + SF (0.1%) | 5 | 5 | — | — |
| MCPP (Na salt) (0.1%) | 1 | 0 | +++ | +++ |

TABLE 8-continued

| | Scales | | | |
|---|---|---|---|---|
| | 21 Days later | | 3 Months later | |
| Test Compounds (Concentration in %) | Ro | Zy | Ro | Zy |
| MCPP (Na salt) (0.2%) | 2 | 0 | +++ | +++ |
| MCPP (Na salt) (0.1%) + SF (0.05%) | 4.5 | 3 | + | + |
| MCPP (Na salt) (0.1%) + SF (0.1%) | 4.5 | 4 | ± | ± |
| MCPP (Na salt) (0.2%) + SF (0.05%) | 5 | 5 | — | — |
| MCPP (Na salt) (0.2%) + SF (0.1%) | 5 | 5 | — | — |
| MCPB (Na salt) (0.1%) | 1 | 0 | +++ | +++ |
| MCPB (Na salt) (0.2%) | 2 | 0 | +++ | +++ |
| MCPB (Na salt) (0.1%) + SF (0.05%) | 4.5 | 3 | + | + |
| MCPB (Na salt) (0.1%) + SF (0.1%) | 4.5 | 4 | ± | ± |
| MCPB (Na salt) (0.2%) + SF (0.05%) | 5 | 5 | — | — |
| MCPB (Na salt) (0.2%) + SF (0.1%) | 5 | 5 | — | — |
| 2,4,5-T (Na salt) (0.1%) | 1 | 0 | +++ | +++ |
| 2,4,5-T (Na salt) (0.2%) | 2 | 0 | +++ | +++ |
| 2,4,5-T (Na salt) (0.1%) + SF (0.05%) | 4.5 | 4 | ± | ± |
| 2,4,5-T (Na salt) (0.1%) + SF (0.1%) | 4.5 | 4 | ± | ± |
| 2,4,5-T (Na salt) (0.2%) + SF (0.05%) | 5 | 5 | — | — |
| 2,4,5-T (Na salt) (0.2%) + SF (0.1%) | 5 | 5 | — | — |
| SL-501 (Na salt) (0.1%) | 0.5 | 2 | +++ | ++ |
| SL-501 (Na salt) (0.2%) | 1 | 3 | +++ | ++ |
| SL-501 (Na salt) (0.1%) + SF (0.05%) | 2.5 | 4 | ++ | — |
| SL-501 (Na salt) (0.1%) + SF (0.1%) | 3.5 | 5 | ++ | — |
| SL-501 (Na salt) (0.2%) + SF (0.05%) | 3.5 | 5 | ± | — |
| SL-501 (Na salt) (0.2%) + SF (0.1%) | 4.5 | 5 | ± | — |
| 2,3,6-TBA (Na salt) (0.1%) | 1 | 0 | +++ | +++ |
| 2,3,6-TBA (Na salt) (0.2%) | 2 | 0 | +++ | +++ |
| 2,3,6-TBA (Na salt) (0.1%) + SF (0.05%) | 4 | 3 | + | + |
| 2,3,6-TBA (Na salt) (0.1%) + SF (0.1%) | 4 | 3 | ± | ± |
| 2,3,6-TBA (Na salt) (0.2%) + SF (0.05%) | 5 | 5 | — | — |
| 2,3,6-TBA (Na salt) (0.2%) + SF (0.1%) | 5 | 5 | — | — |
| Banvel-D (Na salt) (0.1%) | 1 | 0 | +++ | +++ |
| Banvel-D (Na salt) (0.2%) | 2 | 0 | +++ | +++ |
| Banvel-D (Na salt) (0.1%) + SF (0.05%) | 4 | 3 | + | + |
| Banvel-D (Na salt) (0.1%) + SF (0.1%) | 4 | 4 | — | — |
| Banvel-D (Na salt) (0.2%) + SF (0.05%) | 5 | 5 | — | — |
| Banvel-D (Na salt) (0.2%) + SF (0.1%) | 5 | 5 | — | — |
| Amiben (Na salt) (0.1%) | 1 | 0 | +++ | +++ |
| Amiben (Na salt) (0.2%) | 2 | 0 | +++ | +++ |
| Amiben (Na salt) (0.1%) + SF (0.05%) | 4 | 3 | + | + |
| Amiben (Na salt) (0.1%) + SF (0.1%) | 4 | 3 | ± | ± |
| Amiben (Na salt) (0.2%) + SF (0.05%) | 5 | 5 | — | — |
| Amiben (Na salt) (0.2%) + SF (0.1%) | 5 | 5 | — | — |
| TPA (Na salt) (0.1%) | 1 | 0 | +++ | +++ |
| TPA (Na salt) (0.2%) | 2 | 0 | +++ | +++ |
| TPA (Na salt) (0.1%) + SF (0.05%) | 4 | 3 | + | + |
| TPA (Na salt) (0.1%) + SF (0.1%) | 4 | 3 | ± | ± |
| TPA (Na salt) (0.2%) + SF (0.05%) | 5 | 5 | — | — |
| TPA (Na salt) (0.2%) + SF (0.1%) | 5 | 5 | — | — |
| Dowco-233 (Na salt) (0.05%) | 3 | 0 | + | +++ |
| Dowco-233 (Na salt) (0.1%) | 4 | 0 | + | +++ |
| Dowco-233 (Na salt) (0.05%) + SF (0.05%) | 5 | 2.5 | ± | ± |
| Dowco-233 (Na salt) (0.05%) + SF (0.1%) | 5 | 3.5 | ± | ± |
| Dowco-233 (Na salt) (0.1%) + SF (0.05%) | 5 | 5 | — | — |
| Dowco-233 (Na salt) (0.1%) + SF (0.1%) | 5 | 5 | — | — |
| Glyphosate (0.05%) (isopropylamine salt) | 1.5 | 1 | +++ | +++ |
| Glyphosate (0.1%) (isopropylamine salt) | 2.5 | 2 | ++ | ++ |
| Glyphosate (0.05%) + SF (0.05%) (isopropylamine salt) | 4 | 3.5 | + | + |
| Glyphosate (0.05%) + SF (0.1%) (isopropylamine salt) | 5 | 5 | — | — |
| Glyphosate (0.1%) + SF (0.05%) (isopropylamine salt) | 5 | 4.5 | — | — |
| Glyphosate (0.1%) + SF (0.1%) | 5 | 5 | — | — |

TABLE 8-continued

| Test Compounds (Concentration in %) | Scales | | | |
|---|---|---|---|---|
| | 21 Days later | | 3 Months later | |
| | Ro | Zy | Ro | Zy |
| (isopropylamine salt) | | | | |
| DPX-1108 (Na salt) (0.2%) | 0 | 0 | +++ | ++* |
| DPX-1108 (Na salt) (0.4%) | 0 | 0 | +++ | +* |
| DPX-1108 (Na salt) (0.2%) + SF (0.05%) | 2 | 2.5 | + | + |
| DPX-1108 (Na salt) (0.2%) + SF (0.1%) | 3 | 3.5 | ± | ± |
| DPX-1108 (Na salt) (0.4%) + SF (0.05%) | 4.5 | 4.5 | — | — |
| DPX-1108 (Na salt) (0.4%) + SF (0.1%) | 4.5 | 4.5 | — | — |
| NP-48 (0.15%) | 1 | 2 | +++ | ++ |
| NP-48 (0.3%) | 1 | 3.5 | +++ | ++ |
| NP-48 (0.15%) + SF (0.05%) | 2.5 | 4 | ++ | — |
| NP-48 (0.15%) + SF (0.1%) | 3 | 4.5 | + | — |
| NP-48 (0.3%) + SF (0.05%) | 3.5 | 5 | ± | — |
| NP-48 (0.3%) + SF (0.1%) | 4 | 5 | ± | — |
| Linuron (0.1%) | 3 | 2 | +++ | +++ |
| Linuron (0.3%) | 4 | 4 | +++ | +++ |
| Linuron (0.1%) + SF (0.05%) | 5 | 4 | ++ | + |
| Linuron (0.1%) + SF (0.1%) | 5 | 5 | + | + |
| Linuron (0.3%) + SF (0.05%) | 5 | 5 | — | ± |
| Linuron (0.3%) + SF (0.1%) | 5 | 5 | — | — |
| ATA (0.05%) | 2 | 2 | +++ | +++ |
| ATA (0.1%) | 4 | 4 | +++ | +++ |
| ATA (0.05%) + SF (0.05%) | 4 | 4 | — | — |
| ATA (0.05%) + SF (0.1%) | 5 | 5 | — | — |
| ATA (0.1%) + SF (0.05%) | 5 | 5 | — | — |
| ATA (0.1%) + SF (0.1%) | 5 | 5 | — | — |
| Choline hydrochloride (0.1%) | 0 | 0 | +++ | +++ |
| Choline hydrochloride (0.2%) | 0 | 0 | +++ | +++ |
| Choline hydrochloride (0.1%) + SF (0.05%) | 3.5 | 3 | ± | ± |
| Choline hydrochloride (0.1%) + SF (0.1%) | 4.5 | 4 | — | — |
| Choline hydrochloride (0.2%) + SF (0.05%) | 5 | 5 | — | — |
| Choline hydrochloride (0.2%) + SF (0.1%) | 5 | 5 | — | — |
| Diethylamine hydrochloride (0.1%) | 0 | 0 | +++ | +++ |
| Diethylamine hydrochloride (0.2%) | 0 | 0 | +++ | +++ |
| Diethylamine hydrochloride (0.1%) + SF (0.05%) | 3 | 2.5 | + | + |
| Diethylamine hydrochloride (0.1%) + SF (0.1%) | 4 | 3.5 | — | — |
| Diethylamine hydrochloride (0.2%) + SF (0.05%) | 5 | 4.5 | — | — |
| Diethylamine hydrochloride (0.2%) + SF (0.1%) | 5 | 5 | — | — |
| Untreated | 0 | 0 | +++ | +++ |

An anterisk (*) means growth retardation in height.

Table 8 shows that when the SF-1293 substances (A) or the compounds (B) is applied alone separately to *Rumex obtusifolius* and *Zoysia japonica*, there is obtained substantial damage of foliage of these weeds but little suppression of regrowth of these weeds from their underground roots, and that the combined use of the two components (A) and (B) can achieve complete suppression of such regrowth.

EXAMPLE 11

Aqueous solutions containing monosodium salt of SF-1293 substance and CMH, in admixture or separately, and 0.1% of octylphenylpolyoxyethanol as surfactant were applied at a rate of 150 l/10 ares to spontaneously occurring perennial weeds at certain growth stage. Evaluation was made by the same gradings as indicated in Example 10 both for damage to plants (assessed 21 days after treatment) and for suppression of regrowth (assessed 4 months later).

The results are listed in Table 9 below.

TABLE 9

| Test Compounds (Concentration in %) | Scale 21 Days | | | | | | | | | |
|---|---|---|---|---|---|---|---|---|---|---|
| | Pc | Ap | Ro | Cy | Ic | Pr | An | Sc | Cp | Ch |
| SF-1293 (Na salt) (0.05%) | 2 | 4 | 2.5 | 3 | 4 | 3 | 1 | 3 | 1 | 5 |
| SF-1293 (Na salt) (0.1%) | 4 | 5 | 4 | 4 | 5 | 4.5 | 2 | 4 | 2 | 5 |
| SF-1293 (Na salt) (0.2%) | 5 | 5 | 5 | 5 | 5 | 5 | 3 | 5 | 3 | 5 |
| SF-1293 (Na salt) (0.4%) | 5 | 5 | 5 | 5 | 5 | 5 | 4.5 | 5 | 4.5 | 5 |
| CMH (0.3%) | 0 | 1 | 0 | 0 | 0 | 0 | 0 | 0 | 0 | 1 |
| CMH (0.6%) | 2 | 2 | 0 | 1 | 1 | 1 | 0 | 1 | 0 | 3 |
| SF-1293 (Na salt) (0.05%) + CMH (0.3%) | 3.5 | 5 | 4.5 | 4 | 4.5 | 4.5 | 3 | 4 | 2 | 5 |
| SF-1293 (Na salt) (0.05%) + CMH (0.6%) | 4.5 | 5 | 4.5 | 4 | 5 | 5 | 3 | 4 | 2 | 5 |
| SF-1293 (Na salt) (0.1%) + CMH (0.3%) | 5 | 5 | 5 | 4.5 | 5 | 5 | 4 | 5 | 4 | 5 |
| SF-1293 (Na salt) (0.1%) + CMH (0.6%) | 5 | 5 | 5 | 5 | 5 | 5 | 4 | 5 | 4 | 5 |
| SF-1293 (Na salt) (0.2%) + CMH (0.3%) | 5 | 5 | 5 | 5 | 5 | 5 | 5 | 5 | 5 | 5 |
| SF-1293 (Na salt) (0.2%) + CMH (0.6%) | 5 | 5 | 5 | 5 | 5 | 5 | 5 | 5 | 5 | 5 |
| Untreated | 0 | 0 | 0 | 0 | 0 | 0 | 0 | 0 | 0 | 0 |

| Test Compounds (Concentration in %) | Scale 4 Months | | | | | | | | | |
|---|---|---|---|---|---|---|---|---|---|---|
| | Pc | Ap | Ro | Cy | Ic | Pr | An | Sc | Cp | Ch |
| SF-1293 (Na salt) (0.05%) | ++ | + | ++ | +++ | + | ++ | ± | +++ | +++ | +++ |
| SF-1293 (Na salt) (0.1%) | + | — | + | ++ | ± | ± | = | ++ | ++ | ++ |
| SF-1293 (Na salt) (0.2%) | — | — | — | + | ± | ± | = | + | + | + |
| SF-1293 (Na salt) (0.4%) | — | — | — | ± | — | = | = | + | + | + |
| CMH (0.3%) | ++ | ++ | +++ | +++ | +++ | +++ | ++ | ++ | ++ | ++ |
| CMH (0.6%) | + | + | +++ | +++ | +++ | ++ | ++ | ++ | ++ | ++ |
| SF-1293 (Na salt) (0.05%) + CMH (0.3%) | + | — | = | ++ | ± | + | + | + | = | = |
| SF-1293 (Na salt) (0.05%) + CMH (0.6%) | = | — | — | ± | ± | ± | + | + | = | = |
| SF-1293 (Na salt) (0.1%) + CMH (0.3%) | = | — | = | = | = | = | = | = | = | = |
| SF-1293 (Na salt) (0.1%) + CMH (0.6%) | = | = | = | = | = | = | = | = | = | = |
| SF-1293 (Na salt) (0.2%) + CMH (0.3%) | = | = | = | = | = | = | = | = | = | = |
| SF-1293 (Na salt) (0.2%) + CMH (0.6%) | = | = | = | = | = | = | = | = | = | = |

TABLE 9-continued

| Untreated | +++ | +++ | +++ | +++ | +++ | +++ | +++ | +++ | +++ | +++ |

The abbreviations of the test plants are assigned as follows:
Pc: *Pleioblastus chino*
Ap: *Artemisia princeps*
Ro: *Rumex obtusifolius*
Cy: *Cayratia japonica*
Ic: *Imperata cyrindrica*
Pr: *Pueraria lobata*
An: *Athyrium nipinicium*
Sc: *Solanum carolinens*
Cp: *Cyperus rotundus*
Ch: *Calystegia hederacea*

Table 9 clearly shows that the mixture of monosodium salt of SF-1293 substance and CMH leads to remarkable improvement in suppression of regrowth and exhibits a wider spectrum of weed control.

EXAMPLE 12

Formulations in the form of aqueous solutions similar to those used in Example 11 were applied at a rate of 150 l per 10 ares to plants growing in the areas of *Chamaecyparis obtusa*. 30 Days and 3 months after foliage treatment, damage to plants was visually assessed on a scale of 0 to 5 where 0 is no effect and 5 is complete kill as described in Example 6.

The results are set out in Table 10.

TABLE 10

| | Scale | | | | | | | | | |
|---|---|---|---|---|---|---|---|---|---|---|
| | 30 Days | | | | | 3 Months | | | | |
| Test Compounds (Concentration in %) | Ch | Ct | Sa | Ms | Rc | Ch | Ct | Sa | Ms | Rc |
| SF-1293 (Na salt) (0.125%) | 0 | 5 | 3 | 3 | 4 | 0 | 3 | 2 | 2 | 3 |
| SF-1293 (Na salt) (0.25%) | 0 | 5 | 4 | 4 | 4.5 | 0 | 4 | 3 | 3 | 4 |
| SF-1293 (Na salt) (0.5%) | 0 | 5 | 5 | 5 | 5 | 0 | 5 | 4 | 4 | 5 |
| CMH (0.25%) | 0 | 0 | 0 | 0 | 0 | 0 | 0 | 0 | 0 | 0 |
| CMH (0.5%) | 0 | 1 | 1 | 1 | 1 | 0 | 0 | 1 | 0 | 1 |
| CMH (1.0%) | 0 | 3 | 2 | 2 | 2 | 0 | 1 | 2 | 1 | 2 |
| SF-1293 (Na salt) (0.125%) + CMH (0.25%) | 0 | 5 | 4 | 4 | 4.5 | 0 | 5 | 4.5 | 4 | 4.5 |
| SF-1293 (Na salt) (0.125%) + CMH (0.5%) | 0 | 5 | 4 | 4 | 4.5 | 0 | 5 | 5 | 4.5 | 5 |
| SF-1293 (Na salt) (0.125%) + CMH (1.0%) | 0 | 5 | 4.5 | 4 | 4.5 | 0 | 5 | 5 | 5 | 5 |
| SF-1293 (Na salt) (0.25%) + CMH (0.25%) | 0 | 5 | 5 | 4.5 | 5 | 0 | 5 | 5 | 4.5 | 5 |
| SF-1293 (Na salt) (0.25%) + CMH (0.5%) | 0 | 5 | 5 | 5 | 5 | 0 | 5 | 5 | 5 | 5 |
| SF-1293 (Na salt) (0.25%) + CMH (1.0%) | 0 | 5 | 5 | 5 | 5 | 0 | 5 | 5 | 5 | 5 |
| SF-1293 (Na salt) (0.5%) + CMH (0.25%) | 0 | 5 | 5 | 5 | 5 | 0 | 5 | 5 | 5 | 5 |
| SF-1293 (Na salt) (0.5%) + CMH (0.5%) | 0 | 5 | 5 | 5 | 5 | 0 | 5 | 5 | 5 | 5 |
| SF-1293 (Na salt) (0.5%) + CMH (1.0%) | 0 | 5 | 5 | 5 | 5 | 0 | 5 | 5 | 5 | 5 |
| Untreated | 0 | 0 | 0 | 0 | 0 | 0 | 0 | 0 | 0 | 0 |

The names of the test plants are assigned as follows:
Ch: *Chamaecyparis obtusa*
Ct: *Castamea crenata*
Sa: *Sasa nipponica*
Ms: *Miscanthus sinensis*
Rc: *Rubus crataegifolius*

Table 10 demonstrates that the mixture of monosidum salt of the SF-1293 substance and CMH considerably enhances the regrowth-inhibitory effect of the sodium salt but is non-phytotoxic to useful woody plant, *Chamaecyparis obtusa*.

EXAMPLE 13

Formulations in the form of aqueous solutions similar to those used in Example 11 were applied at a rate of 100 l per 10 ares to spontaneously occurring weeds, *Echinochloa crusgali* (abbreviated as Ec) and *Digitaria adscendens* (abbreviated as Dg) at intermediate growth stage. 14 Days and one month after foliage treatment, damage to plants was assessed. Besides, one month after treatment, degree of suppression of regrowth was evaluated, by the same gradings as indicated in Example 11.

The test results are shown in Table 11.

TABLE 11

| | Scale | | | | |
|---|---|---|---|---|---|
| | 14 Days | | 1 Month | | |
| Test Compounds (Concentration in %) | Ec | Dg | Ec | | Dg |
| SF-1293 (Na salt) (0.05%) | 3 | 3 | 1 | +++ 1 | +++ |
| SF-1293 (Na salt) (0.1%) | 4 | 4 | 3 | ++ 3 | ++ |
| SF-1293 (Na salt) (0.2%) | 5 | 5 | 4 | ± 4 | ± |
| CMH (0.3%) | 0 | 0 | 0 | +++ 0 | +++ |
| CMH (0.6%) | 1 | 1 | 0 | +++ 0 | +++ |
| SF-1293 (Na salt) (0.5%) + CMH (0.3%) | 4 | 4 | 4 | ± 4 | ± |
| SF-1293 (Na salt) (0.5%) + CMH (0.6%) | 4 | 4 | 4.5 | ± 4.5 | ± |
| SF-1293 (Na salt) (0.1%) + CMH (0.3%) | 5 | 5 | 5 | — 5 | — |
| SF-1293 (Na salt) (0.1%) + CMH (0.6%) | 5 | 5 | 5 | — 5 | — |
| SF-1293 (Na salt) (0.2%) + CMH (0.3%) | 5 | 5 | 5 | — 5 | — |
| SF-1293 (Na salt) (0.2%) + CMH (0.6%) | 5 | 5 | 5 | — 5 | — |
| Untreated | 0 | 0 | 0 | +++ 0 | +++ |

EXAMPLE 14

The area where various bushes and weeds were spontaneously growing was divided into plots of each 4 m², which was sprayed in autamn season evenly at a rate of 150 l per 10 ares with aqueous solutions containing sodium salt of SF-1293 substance and CMH, in admixture or separately, and containing further 0.1% of octylpheneylpolyoxyethanol as surfactant. 7 Months after spraying, namely at the end of the next spring season, damage to plants was visually assessed on a scale of 0 to 5 where 0 indicates no effect and 5 indicates complete kill as well as complete suppression of regrowth.

The results are shown in Table 12.

TABLE 12

| Test Compounds (Concentration in %) | Damage Scale | Remarks |
|---|---|---|
| SF-1293 (Na salt) | 3.5 | Hd 5, Fr 3, Rh 5, Pc 4.5 |

TABLE 12-continued

| Test Compounds (Concentration in %) | Damage Scale | Remarks |
|---|---|---|
| (0.125%) | | |
| SF-1293 (Na salt) (0.25%) | 4.5 | Qu 5, Cb 4.5, Fr 4 |
| SF-1293 (Na salt) (0.5%) | 5 | Hd 5, Cb 5, Rh 5 |
| CMH (0.5%) | 0.5–1 | Cb 0.5, Rh 1.5–2, Hm 1.5 |
| CMH (1.0%) | 1 | Qu 3.5–4, Rh 3.5–4, Cb 0.5 Slight damage to other plants |
| CMH (2.0%) | 1–1.5 | Ct 3.5–4, Cb 1, Rt 1 Slight damage to other plants |
| SF-1293 (Na salt) (0.125%) + CMH (0.5%) | 4.5 | Pc 4.5–5 No substantial regrowth of Sy and Hm |
| SF-1293 (Na salt) (0.125%) + CMH (1.0%) | 4.5 | No substantial regrowth of Ln, Rh and Pc |
| SF-1293 (Na salt) (0.125%) + CMH (2.0%) | 5 | Great damage to Pc, Fr, Hd, Am and others |
| SF-1293 (Na salt) (0.25%) + CMH (0.5%) | 4.5 | No substantial regrowth of Cb, Rh, Pc and Fr |
| SF-1293 (Na salt) (0.25%) + CMH (1.0%) | 5 | No regrowth of Fr, Rh and Cb |
| SF-1293 (Na salt) (0.25%) + CMH (2.0%) | 5 | No regrowth |
| SF-1293 (Na salt) (0.5%) + CMH (0.5%) | 5 | No regrowth |
| SF-1293 (Na salt) (0.5%) + CMH (1.0%) | 5 | No regrowth |
| SF-1293 (Na salt) (0.5%) + CMH (2.0%) | 5 | No regrowth |
| Untreated plot (Height of plants) | 0 | Hd 30 cm, Ln 20 cm, Cb 50 cm Pc 75 cm, Rh 10–20 cm, Fr 25 cm |

The names of the test plants are assigned as follows:
Hd: Hydrangea hirta
Fr: Fraxinus japonica
Rh: *Rhododendron kaempferi*
Pc: *Pleioblastus chino*
Qu: *Quercus grossesenata*
Cb: *Clethra barbinervis*
Hm: *Hamamelis japonica*
Ct: *Castanea crenata*
Rt: *Rhus trichocarpa*
Sy: *Styrax japonica*
Ln: *Lyonia neziki*
Am: *Acer mono*

EXAMPLE 15

In order to evaluate the herbicidal effect of the SF-1293 substances against evergreen bushes, aqueous solutions similar to those used in Example 14 were applied at a rate of 100 l per 10 ares to *Ternstroemia gymnanthera*, *Ligustrum japonicum* and *Rhaphiolepis umbellata* (abbreviated as Tr, Lg and Ru, respectively). 5 Months after foliage treatment, damage to plants was visually assessed by the same gradings as indicated in Example 14.

The test results are tabulated in Table 13.

TABLE 13

| Test Compounds + (Concentration in %) | Scale Lg | Tr | Ru |
|---|---|---|---|
| SF-1293 Na salt (0.25%) | 4.5 | 5 | 5 |
| SF-1293 Na salt (0.5%) | 5 | 5 | 5 |
| CMH (0.5%) | 2 | 2 | 2 |
| CMH (1.0%) | 3 | 2.5 | 2.5 |
| CMH (2.0%) | 3.5 | 3 | 3 |
| SF-1293 Na salt (0.25%) + CMH (0.5%) | 5 | 5 | 5 |
| SF-1293 Na salt (0.25%) + CMH (1.0%) | 5 | 5 | 5 |
| SF-1293 Na salt (0.25%) + CMH (2.0%) | 5 | 5 | 5 |
| SF-1293 Na salt (0.5%) + CMH (0.5%) | 5 | 5 | 5 |
| SF-1293 Na salt (0.5%) + CMH (1.0%) | 5 | 5 | 5 |
| SF-1293 Na salt (0.5%) + CMH (2.0%) | 5 | 5 | 5 |
| Untreated | 0 | 0 | 0 |

EXAMPLE 16

Aqueous solutions comprising sodium salt of SF-1293 substance as active ingredient and 0.1% of octylphenyl-polyoxyethanol as surfactant were applied at a rate of 100 l/10 ares to *Cyperus serotinus* grown in a Wagner porcelain pot of 1/5000 a in cross-section. The pot thus treated was allowed to stand outdoors for about 3 months. Then, the tubers was taken from the underground soil in the pot and transferred into a deep petri dish. The dish was placed in the greenhouse for emergence. 21 Days later, evaluation was made for prevention of emergence on a scale of 0 to 5 where 0 is no effect and 5 is complete prevention of emergence.

The results are shown in Table 14.

TABLE 14

| Test Compounds (Concentration in %) | Degree of Prevention of Emergence |
|---|---|
| SF-1293 (Na salt) (0.1%) | 5 |
| SF-1293 (Na salt) (0.3%) | 5 |
| Glyphosate (isopropylamine salt) (0.1%) (Control) | 5 |
| Glyphosate (isopropylamine salt) (0.3%) (Control) | 5 |
| Untreated | 0 |

What we claim is:

1. A process for severely damaging or killing unwanted herbaceous and woody plants, which comprises applying to plants susceptible thereto a herbicidally effective amount of SF-1293 substance or an alkali metal, alkaline earth metal, copper, zinc, nickel, manganese, ammonium, substituted ammonium or acid-addition salt thereof, said SF-1293 substance or salt thereof being of the formula:

$$\left[ \begin{array}{c} H_3C \quad O \\ \diagdown \; \| \\ P-CH_2-CH_2-CH-CONH- \\ \diagup \\ (M^1)pO \end{array} \right. \quad \begin{array}{c} \\ \\ | \\ NH_2 \end{array}$$

$$\left. \begin{array}{c} -CH-CONH-CH-COO(M^2)q \\ | \qquad\qquad\qquad | \\ CH_3 \qquad\qquad\qquad CH_3 \end{array} \right] nA$$

wherein $M^1$ and $M^2$ are each hydrogen or a cation selected from the group consisting of sodium, potassium, lithium, copper, magnesium, calcium, zinc, nickel, maganese and ammonium which is unsubstituted or substituted by 1–4 lower alkyl, hydroxy lower alkyl, or lower alkenyl; A is an inorganic or organic acid selected from the group consisting of hydrochloric, sulfuric, hydrobromic, phosphoric, perchloric, nitric, acetic, propionic, citric, tartaric, monochloroacetic, trichloroacetic and trifluoroacetic acids; n is 0, 0.5 or 1; p is the inverse number of the valency of $M^1$; and q is the inverse number of the valency of $M^2$.

2. A process according to claim 1 in which the SF-1293 substance is a salt selected from the group consisting of the monosodium, disodium, monopotassium, dipotassium, mono(diethanolamine), mono(isopropylamine), mono(dimethylamine) and mono(n-butylamine) salts thereof.

3. A process according to claim 1 for selectively controlling the growth of unwanted weeds and bushes in an area of useful woody plants, *Chamaecyparis obtusa*, an orchard or forestry land, wherein the SF-1293 substance or salt thereof is applied in an amount sufficient to inhibit growth of the unwanted weeds and bushes but insufficient to substantially harm the desired plants.

* * * * *